(12) United States Patent
Townsend et al.

(10) Patent No.: US 7,603,165 B2
(45) Date of Patent: *Oct. 13, 2009

(54) METHOD FOR ACQUIRING PET AND CT IMAGES

(75) Inventors: David W. Townsend, Pittsburgh, PA (US); Ronald Nutt, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 864 days.

This patent is subject to a terminal disclaimer.

(21) Appl. No.: 10/623,437

(22) Filed: Jul. 18, 2003

(65) Prior Publication Data

US 2004/0030246 A1  Feb. 12, 2004

Related U.S. Application Data

(60) Division of application No. 10/167,837, filed on Jun. 12, 2002, now Pat. No. 6,631,284, which is a continuation-in-part of application No. 09/685,222, filed on Oct. 10, 2000, now Pat. No. 6,490,476.

(60) Provisional application No. 60/159,395, filed on Oct. 14, 1999.

(51) Int. Cl.
*A61B 6/00* (2006.01)

(52) U.S. Cl. .......................... 600/427; 600/436; 378/4; 250/363.03; 250/363.04

(58) Field of Classification Search ................. 600/427, 600/436; 378/4, 21, 209; 250/363.03, 363.04
See application file for complete search history.

(56) References Cited

U.S. PATENT DOCUMENTS 5,376,795 A  12/1994  Hasegawa et al.
5,969,358 A * 10/1999  DiFilippo et al. ...... 250/363.03
6,205,347 B1  3/2001  Morgan et al.
6,339,223 B1 * 1/2002  Motomura et al. ..... 250/363.07

OTHER PUBLICATIONS

Beyer et al., "The use of X-ray CT for Attenuation Correction of PET Data," IEEE, Mar. 1995, pp. 1573-1577.

A.C. Evans, et al., "MRI-PET Correlation in Three Dimensions Using a Volume-of-Interest (VOI) Atlas," Journal of Cerebral Blood Flow & Metabolism, A69-A78, 1991.

D.G. Thomas et al., "Use of relocatable stereotactic frame to integrate positron emission tomography and computed tomography images: application to human malignant brain tumors," Stereotactic and Functional Neurosurgery, 388-392, 1990.

(Continued)

Primary Examiner—Ruth S Smith

(57) ABSTRACT

A combined PET and X-Ray CT tomograph for acquiring CT and PET images sequentially in a single device, overcoming alignment problems due to internal organ movement, variations in scanner bed profile, and positioning of the patient for the scan. In order to achieve good signal-to-noise (SNR) for imaging any region of the body, an improvement to both the CT-based attenuation correction procedure and the uniformity of the noise structure in the PET emission scan is provided. The PET/CT scanner includes an X-ray CT and two arrays of PET detectors mounted on a single support within the same gantry, and rotate the support to acquire a full projection data set for both imaging modalities. The tomograph acquires functional and anatomical images which are accurately co-registered, without the use of external markers or internal landmarks.

20 Claims, 6 Drawing Sheets

OTHER PUBLICATIONS

C.A. Pelizzari et al., "Accurate three-dimensional registration of CT, PET and MR images of the brain," J Comp Assist Tomogr, 2026, 1989.

R.P. Woods et al., "Rapid automated algorithm for aligning and reslicing PET images," J Comp Assist Tomogr, 620-633, 1992.

R.P. Woods et al., "MRI-PET registration with an automated algorithm," J Comp Assist Tomogr, 536-546, 1993.

U. Peitrzyk et al., "Three-dimensional alignment of functional and morphological tomograms," J Comp Assist Tomogr, 51-59, 1990.

R. L. Wahl et al., "Anatometabolic' tumor imaging: fusion of FDG PET with CT or MRI to localize foci of increased activity," J. NUcl. Med., 1190-1197, 1993.

T.F. Lang et al., "A prototype emission-transmission imaging system," IEEE Nucl. Sci., Symposium Conf. Record, 1902-1906, 1991.

T.F. Lang et al., "Description of a prototype emission-transmission computed tomography imaging system," J. Nucl. Med., 1881-1887, 1992.

J.S. Fleming, "A technique for using CT images in attenuation correction and quantification in SPECT," Nucl. Med. Commun, 83-97, 1989.

S.C. Moore, "Attenuation compensation" in Ell, P.J. et al., Computed Emission Tomography, London, Oxford University Press, 339-360, 1982.

B.H. Hasegawa et al., "Object specific attenuation correction of SPECT with correlated dual-energy X-ray CT," IEEE Trans. Nucl. Sci., 1242-1252, 1993.

K.J. LaCroix et al., "Investigation of the use of X-ray CT images for attenuation compensation in SPECT," IEEE 1993 Medical Imaging Conference Record, 1994.

S.C. Huang et al., "Quantitation in positron emission tomography: 2. Effects of inaccurate attenuation correction," J. Comput Assist Tomogr, 804-814, 1979.

W.F. Jones et al., "Optimizing rod window width in positron emission tomography," IEEE 1992 Medical Imaging Conference Record, 982-984, 1993.

R.A. de Kamp et al., "Attenuation correction in Pet using single photon transmission measurement," Med. Phys., 771-778, 1994.

Qu He et al., "Attenuation correction in PET using a singles transmission source," J. Nucl Med., 41P, 1994.

R.E. Alvarez et al., "Energy-selective reconstructions in X-ray computerized tomography," Phys Med Biol., 733-744, 1976.

D.E. Avrin et al., "Clinical applications of Compton and photoelectric reconstruction in computed tomography: preliminary results," Invest Radiol, 217-222, 1978.

M. Bergstrom et al., "Correction for scattered radiation in a ring detector positron camera by integral transform of the projections," J. Comput. Assist. Tomogr., 42-50, 1983.

M. Endo et al., "Sofware correction of scatter coincidence in positron CT," Eur. J. Nucl. Med., 391-396, 1984.

S.R. Cherry et al., "Correction and characterization of scattered events in three dimensional PET using scanner with retractable septa," J Nucl Med, 671-678, 1993.

D.L. Bailey et al., "A convolution-subtraction scatter correction method for 3D PET," Phys Med Biol., 412-424, 1994.

D. Gagnon et al., "Introduction to holospectral imaging in nuclear medicine for scatter subtraction," IEEE Trans Med Imaging, 245-250, 1989.

S. Grootoonk et al., "Correction for scatter using a dual energy window technique with a tomograph operating without septa," IEEE 1991 Medical Imaging Conference Record, 1569-1573, 1992.

B. Bendriem, et al., "A PET scatter correction using simultaneous acquisitions with low and high lower energy thresholds," IDDD 1993 Medical Imaging Conference Record, 1779-1783, 1994.

J.M. Ollinger, "Model-based scatter correction for fully 3D PET," Phys Med Biol., 153-176, 1996.

C.C. Watson, D. Newport, and M.E. Casey, "A single scatter simulation technique for scatter correction in 3D PET" in: Grangeat P and J-L Amans, Three Dimensional Image Reconstruction in Radiology and Nuclear Medicine, Dordrecht: Kluwer Academic, 255-268, 1996.

R. Leahy et al., "Incorporation of anatomical MR data for improved functional imaging with PET," Information Processing in Medical Imaging, XIIth IPMI International Cnference Record, 1201-1203, 1993.

Z. Zhou et al., "A comparative study of the effects of using anatomical priors in PET reconstruction," IEEE 1993 Medical Imaging Conference Record, 1749-1753, 1994.

Blankespoor et al., "Attenuation Correction of SPECT Using X-Ray CT on an Emission-Transmission CT System: Myocardial Perfusion Assessment," IEEE Transactions on Nuclear Science, Aug. 1996, pp. 2263-2274, vol. 43, No. 4.

Blankespoor et al., "Development of an Emission-Transmission CT System Combining X-Ray CT and SPECT," IEEE, Mar. 1995, pp. 1758-1761.

* cited by examiner

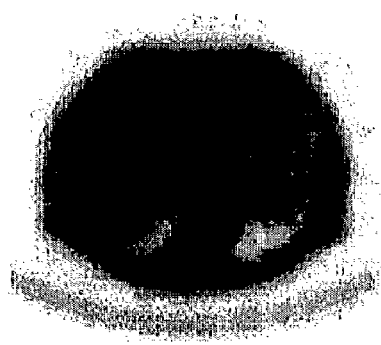
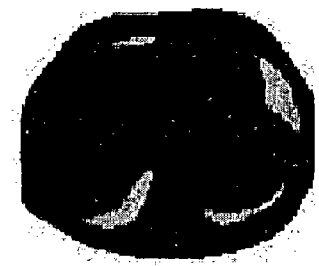
Fig.1a          Fig.1b
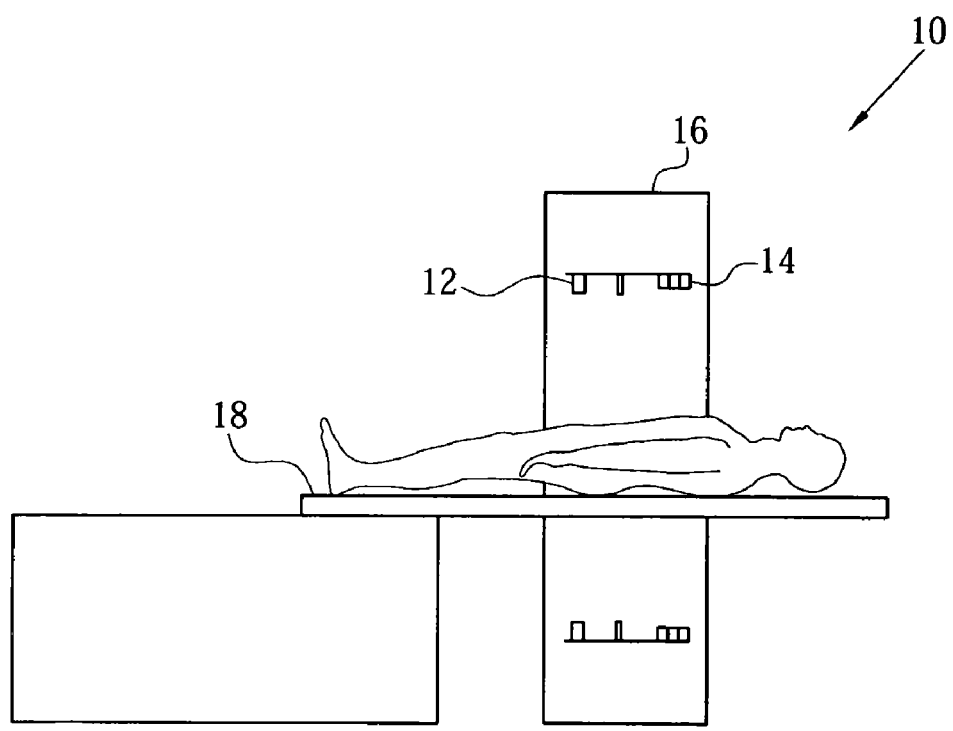
Fig.2a

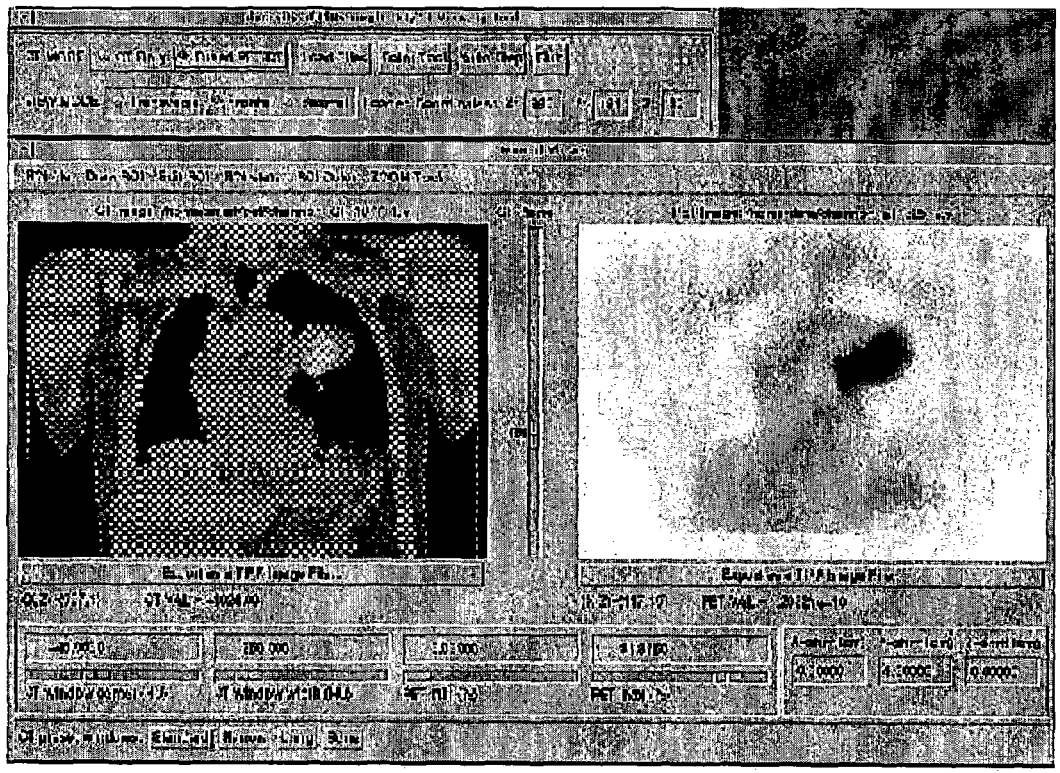
Fig.3
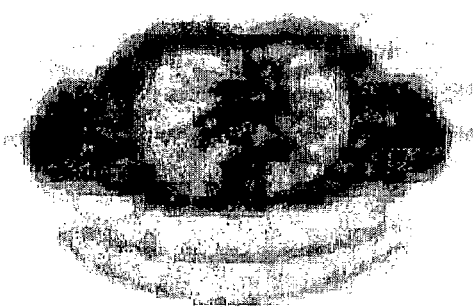 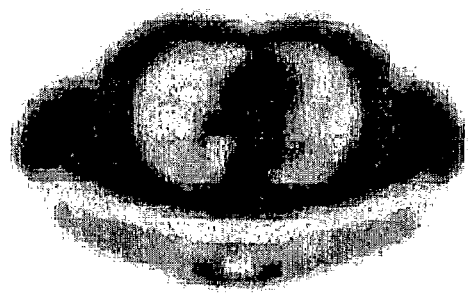
Fig.4a　　　　　　　Fig.4b

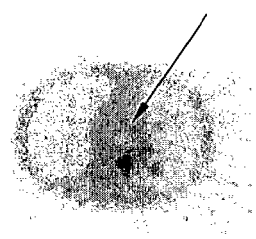 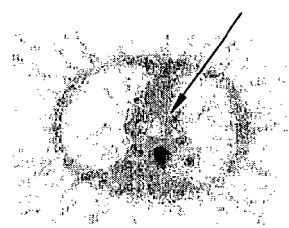
Fig.8a  Fig.8b
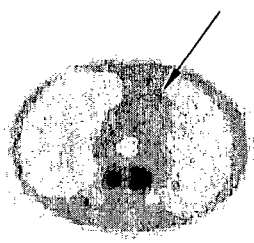 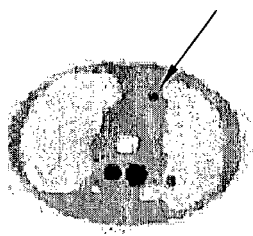 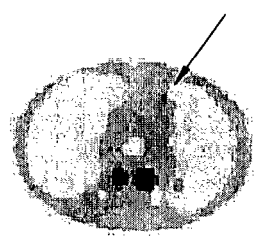
Fig.9a  Fig.9b  Fig.9c

 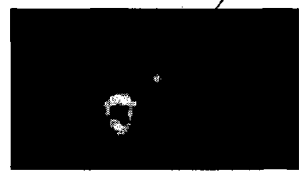 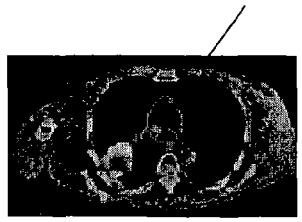
Fig.10a  Fig.10b  Fig.10c
 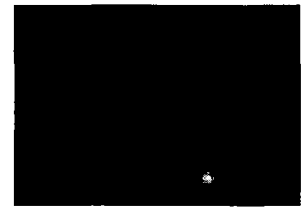 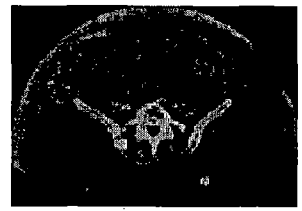
Fig.11a  Fig.11b  Fig.11c
 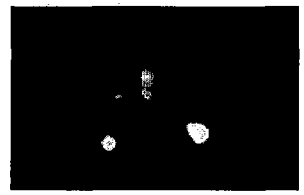 
Fig.12a  Fig.12b  Fig.12c
 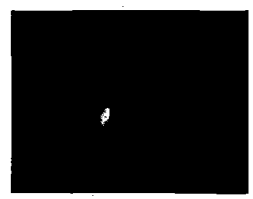 
Fig.13a  Fig.13b  Fig.13c

METHOD FOR ACQUIRING PET AND CT IMAGES

CROSS-REFERENCE TO RELATED APPLICATIONS

This is a division of application Ser. No. 10/167,837, filed Jun. 12, 2002, now U.S. Pat. No. 6,631,284, which is a continuation-in-part of our earlier filed application Ser. No. 09/685,222, filed Oct. 10, 2000, which issued as U.S. Pat. No. 6,490,476, on Dec. 3, 2002, and which claimed the benefit of U.S. Provisional Application No. 60/159,395, filed Oct. 14, 1999.

STATEMENT REGARDING FEDERALLY SPONSORED RESEARCH OR DEVELOPMENT

Not Applicable

BACKGROUND OF THE INVENTION

1. Field of Invention

This invention relates to a tomograph which has the capability of operating in either X-Ray computerized tomography (CT) or positron emission tomography (PET) mode. More specifically, it relates to a combined PET and CT scanner which allows co-registered CT and PET images to be acquired sequentially in a single device, overcoming alignment problems due to internal organ movement, variations in scanner bed profile, and positioning of the patient for the scan.

2. Description of the Related Art

The role of PET imaging in oncology research and patient care is growing. The ability of PET to add unique functional information to that obtained by conventional anatomical-based modalities, such as CT and magnetic resonance (MR), is generating considerable interest. For space-occupying lesions in the head, chest, abdomen and pelvis, one of the best documented applications of PET is in the discrimination of benign from malignant causes. Thus far, $^{18}$F-fluorodeoxyglucose (FDG) has been used to image the distribution of glucose uptake in all of these applications. The increased glucose metabolism of the neoplasm has been used for several purposes. Specific applications include, among other things, determining the presence of recurrent glioma versus radiation necrosis, determining the presence of recurrent colon carcinoma versus surgical scar and radiation changes, determining the presence of pancreatic cancer versus pancreatitis, determining the presence of malignant solitary pulmonary nodules versus benign nodules, and determining the presence of metastatic lung carcinoma versus reactive lymph node.

Some centers are investigating the use of quantitative analysis to increase specificity of FDG uptake. Others are expanding the tumor types that can be characterized. In addition, the development of other radiotracers which image different aspects of tumor metabolism and growth add a further dimension to this research activity. These tracers include $^{11}$C-methionine to measure amino acid incorporation, $^{18}$F-thymidine to measure nucleotide incorporation (a measure of cell proliferation), and $^{18}$F-fluoromisonidazole to measure tissue hypoxia. These alternative imaging possibilities have prompted new investigations to determine whether physiological changes early after chemotherapy or radiation treatment can be seen by PET and used to provide predictions of tumor response.

Another increasingly important application of FDG in oncology is for whole-body scans. Using this technique to stage cancer, occult metastatic disease in almost any region of the body can potentially be detected by increased FDG accumulation. The sensitivity of this approach to small lesions, however, is unclear and may depend on accurate transmission information which is often time-consuming to obtain in whole-body mode.

Finally, the PET imaging of tumor masses, and particularly complex tumor masses with areas of cystic changes, necrosis, or surrounding edema, could potentially be used to guide diagnostic biopsies. In the head, this has been demonstrated to be fairly successful, but extracranial applications have not yet been studied systematically. While accuracy and reliability of CT-guided biopsies is high overall, typically greater than ninety percent (90%), it is known that this accuracy and reliability falls considerably to approximately eighty percent (80%) in the setting of complex lesions in presacral or retroperitoneal locations. Thus, functional knowledge of tumor metabolism would be helpful in better selecting an exact biopsy site in these conditions if correctly registered to CT data.

In recent years, there has been considerable progress in the development of techniques to co-register and align functional and anatomical images. This has been driven primarily by the demand for accurate localization of cerebral function visualized in PET studies where the low resolution morphology is, in most cases, insufficient to identify the related cerebral structures. Techniques to overcome this problem have been developed based, for example, on the identification of certain geometrical features common to both imaging modalities. For example, A. C. Evans et al., *J Cereb Blood Flow Metab* 11(2), A69-A78 (1991) teach the use of landmark matching while D. G. Thomas et al., "Use of relocatable stereotactic frame to integrate positron emission tomography and computed tomography images: application to human malignant brain tumors," *Stereotactic and Functional Neurosurgery* 54-55, 388-392 (1990) teach the use of externally-placed reference or fiducial markers. Identification of the skull and brain contour from either the PET transmission or emission scan and the MR or CT scan has also been employed as an alignment technique by C. A. Pelizzari et al, "Accurate three-dimensional registration of CT, PET and MR images of the brain," *J Comp Assist Tomogr* 13, 2026 (1989). Following the identification of common structures in the two modalities, a rigid-body transformation is used to rotate and translate the MR or CT scan into the reference frame of the PET image, accounting for differences in pixel size between the two imaging modalities. A technique which uses a least squares approach to minimize the distribution of pixel-to-pixel ratios between the two images requiring alignment has proved successful both for PET to PET by R. P. Woods et al., "Rapid automated algorithm for aligning and reslicing PET images," *J Comp Assist Tomogr* 16, 620-633 (1992); and PET to MR by R. P. Woods et al., "MRI-PET registration with an automated algorithm," *J Comp Assist Tomogr* 17, 536-546 (1993). An interactive method has also been published by U. Pietrzyk et al., "Three-dimensional alignment of functional and morphological tomograms," *J Comp Assist Tomogr* 14(1), 51-59 (1990), wherein a human observer makes alignment decisions based on visual inspection of images of brain sections displayed on a computer screen.

After two images from different modalities are aligned, they can be displayed in a number of ways, such as, for example, side by side with linked cross-hair cursors so that positional correspondence between the two image sets is easily established. This type of software tool is now readily available commercially. A different technique that is more appropriate for this project is that of image fusion, in which the two different image sets are combined into a single image so that positional correspondence is automatically established. Fusion techniques in general consist of either statistical methods or color-wash methods. Color-wash methods assign a color scale to one image and an intensity scale to the other image, whereas statistical methods select the most significant values from each image and assign as many orthogonal colors to each as possible for the particular display device.

Essentially all the registration techniques mentioned above have been developed for use in cerebral studies, and in particular brain activation. This is to some extent because PET images of cerebral flow and metabolism already contain a limited amount of low-resolution anatomical information which can be effectively exploited by the alignment procedures. However, the problems of alignment and co-registration in other regions of the human body are more difficult to solve owing to the absence of even low-resolution morphology in the functional image. This is particularly acute in the abdomen, where the PET emission scan shows little or no anatomical detail. Furthermore, the advantage of co-registering organs other than the brain has been recognized only recently, with, as described above, a rapid growth in the use of FDG in oncology.

It is evident, therefore, that in regions such as the thorax and abdomen, the demonstration of increased FDG uptake is limited in value without an unambiguous localization of tracer uptake to a specific structure (e.g., a tumor) seen on the corresponding CT image. It is desirable, therefore, to accomplish accurate registration of anatomical data, such as is obtained with CT, to improve the use of PET imaging in all of the above applications in oncology. In the discrimination of a benign versus a malignant mass, a CT scan typically defines the borders of the mass and co-registration with PET allows a more accurate quantitative evaluation. In certain organs, where nearby structures have a high concentration of excreted tracers, such as FDG in the renal pelvis, exact registration of PET and CT allows a finer discrimination of the etiology of a "hot spot", thus reducing the likelihood of falsely identifying the mass as a tumor, or misjudging a focal accumulation of tracer as probable urine activity. For future tracers which may have labeled metabolites excreted via the hepatobiliary system and bowel, this may be even more crucial.

In "'Anatometabolic' tumor imaging: fusion of FDG PET with CT or MRI to localize foci of increased activity," *J. Nucl. Med.* 34, 1190-1197 (1993), R. L. Wahl et al., disclose the alignment of CT scans with PET FDG functional images and have thus demonstrated the importance of combining anatomy and function in organs other than the brain. Wahl et al., concentrated on tumors in the thoracic and abdominal regions using both external markers and, in the thorax, internal anatomical landmarks such as the carina. Functional and anatomical images were aligned to within an error of magnitude of 5-6 mm, allowing more precise information to be obtained on the extent of the tumoral involvement of surrounding soft tissues than would have been possible from the PET scan alone. This work has also highlighted the difficulties of aligning organs which are not rigidly attached within the body. While the brain remains fixed in the skull, the position of organs such as the liver may depend upon the precise way in which the patient lies on the bed. Thus, PET-CT post-hoc alignment may be affected by different internal relationships and deformations within the body, limiting the accuracy of such an approach.

As is well-known, compared to anatomical imaging modalities, SPECT images are photon-limited and generally lack anatomical landmarks, thus making image alignment, and the definition of regions-of-interest, even more of a problem than it is for PET. In addition, non-uniform photon attenuation introduces distortions and artifacts into the reconstructed images. A prototype hybrid CT/SPECT scanner has been developed to address these issues. As discussed by T. F. Lang et al., "A prototype emission-transmission imaging system," *IEEE Nucl. Sci. Symposium Conf. Record* 3, 1902-1906 (1991); and T. F. Lang et al., "Description of a prototype emission-transmission computed tomography imaging system," *J. Nucl. Med.* 33, 1881-1887 (1992), this device employs the same one-dimensional array of high-purity germanium detectors for both CT and single photon imaging. A goal of the CT/SPECT project is also to use the X-ray CT image to provide the attenuation factors to correct the SPECT data, as suggested by J. S. Fleming, "A technique for using CT images in attenuation correction and quantification in SPECT," *Nucl. Med. Commun* 10, 83-97 (1989). The use of CT images for attenuation correction had been originally proposed by S. C. Moore, "Attenuation compensation" in Ell, P. J. et al., *Computed Emission Tomography*, London, Oxford University Press, 339-360 (1982). The 100 kVp X-ray source is capable of producing a dual-energy X-ray beam, such that an energy-corrected attenuation map can be obtained for use with the radionuclide data, as disclosed by B. H. Hasegawa et al., "Object specific attenuation correction of SPECT with correlated dual-energy X-ray CT," *IEEE Trans. Nucl. Sci.* NS-40 (4), 1242-1252 (1993). Operating the device with two energy windows also allows simultaneous emission-transmission acquisitions to be performed, although the authors report a certain level of contamination of the emission scan by the transmission X-ray beam. This disclosure demonstrates the potential of a device capable of performing both anatomical and functional measurements. It has also given rise to a detailed simulation study to investigate the different techniques for scaling the attenuation coefficients from CT energies (50-80 keV) to SPECT (140 keV). See K. J. LaCroix et al., "Investigation of the use of X-ray CT images for attenuation compensation in SPECT," *IEEE 1993 Medical Imaging Conference Record* (1994).

While the attenuation correction for PET is of a greater magnitude than for SPECT, it is theoretically more straightforward. However, since it is generally based on patient measurements (a transmission scan), it introduces additional noise into the reconstructed emission scan. In practice, in order to limit the duration of the PET scan procedure, abdominal transmission scans of 10-15 minutes are typical, during which 100 million counts are acquired (3 million per slice, or 100 counts per coincidence line of response, i.e. a 10% statistical accuracy), which introduces significant noise into the corrected emission scan. In practice, only lines-of-response (LOR's) through the patient contain useful transmission information, and since some of the coincidence events will lie in LOR's which do not pass through the patient, the total useful counts in a transmission scan is often less than 100 million. In addition, patient movement between the transmission and emission scan (which may be acquired 40 minutes or so later) can introduce serious artifacts and distortions into the reconstructed image, as disclosed by S. C. Huang et al., "Quantitation in positron emission tomography: 2. Effects of inaccurate attenuation correction," *J Comput Assist Tomogr* 3, 804-814 (1979).

FIGS. 1A and 1B illustrate a PET transmission image and a CT image, respectively, for the same transaxial section through a patient. As illustrated in these figures, the statistical noise in a CT image is considerably less than that in an image formed from a PET transmission scan, due to the much higher photon flux available in CT scans. A CT image is formed from a photon flux equivalent to $10^{10}$-$10^{11}$ photons, compared with the $\sim 10^6$ photons/slice in a PET transmission scan.

In a typical PET transmission scanning procedure, the PET transmission scan is performed pre-injection, while the emission scan is performed 45 minutes post-injection, which is potentially a significant source of error if there is any patient motion during this period.

In the above, only the effect of statistical noise introduced into the emission scan by the finite statistics of the transmission scan has been considered. However, there is also an important systematic component to the noise due to the level of scatter in the transmission scan. In a full-ring scanner with rotating rod sources, the position of the sources are monitored and only detected coincidence events which pass close to one of the rods are accepted. W. F. Jones et al., in "Optimizing rod window width in positron emission tomography," *IEEE 1992 Medical Imaging Conference Record* 2, 982-984 (1993), disclose this procedure, which is known as rod windowing. This eliminates much of the scatter, with the possible exception of very small angle scatters. Scatter contamination in the transmission scan results in an underestimate of the linear attenuation coefficients, and a consequent under-correction of the emission scan. In the brain, the tissue attenuation coefficient is underestimated by 12% compared with the known value for 511 keV photons in water.

R. A. de Kemp et al., in "Attenuation correction in PET using single photon transmission measurement," *Med. Phys.* 21, 771-778 (1994); and Qu He et al., in "Attenuation correction in PET using a singles transmission source," *J Nucl Med* 35 (5), 41P (1994), performed studies using an orbiting point source of 511 keV photons for transmission scanning. In this approach only singles are detected, with the position of the source providing the second point on the line-of-response. The statistics in the transmission scan is greatly increased due to the high singles/coincidence ratio, and the fact that the rate is limited by the deadtime of the detector close to the source. However, this study fails to address the problem of scatter in the singles transmission scan for quantitative PET imaging.

The PET attenuation correction factor $\exp\{\int dt \mu_E(t)\}$ is the line integral of the linear attenuation coefficient for each coincidence channel, where E is the photon energy and t is the spatial coordinate along the channel. The attenuation coefficient $\mu_E(x)$ is energy-dependent, and determination of these factors at one energy requires scaling if they are to be used to correct emission data at a different energy. There are two difficulties with scaling CT attenuation factors for use with PET data. Specifically, the annihilation photons used by PET are monoenergetic 511 keV whereas the X-ray source used in CT emits photons which cover a relatively broad spectrum from 40 keV to 120 keV. Second, the attenuation at CT-energies is a combination of both Compton scattering and photoelectric absorption, while at 511 keV the contribution of photoelectric absorption even in bone is essentially negligible.

Solutions to these problems for SPECT applications has been reported, focusing on two approaches to transform $\mu_E(x)$ from the lower energy at which it is measured to the higher energy at which it is required. The first approach, investigated in simulations by LaCroix et al. (1994), scales $\mu_E(x)$ from an effective CT photon energy level in the range of 50-80 keV up to SPECT photon energy level of 140 keV by using a single scaling factor given by the ratio of the attenuation for water at the two energies. While this is a good approximation when the major contribution to $\mu_E(x)$ comes from Compton interactions, it is, however, a poor approximation when photoelectric contributions dominate, as they do at CT energies. The error is particularly large for higher Z materials, such as bone, which contains a large percentage of calcium.

The second and more technically-challenging approach, is to acquire the CT image at two different photon energies—for example, 40 keV and 80 keV—and use these data to extract the individual photoelectric and Compton contributions to $\mu_E(x)$. See R. E. Alvarez et al., "Energy-selective reconstructions in X-ray computerized tomography," *Phys Med Biol* 21(5), 733-744 (1976); and D. E. Avrin et al., "Clinical applications of Compton and photo-electric reconstruction in computed tomography: preliminary results," *Invest Radiol* 13, 217-222 (1978). The different contributions are then scaled in energy separately. The Compton contribution decreases linearly while the photoelectric contribution decreases rapidly as $1/E^3$. The two separate contributions can be scaled independently and combined to form a monoenergetic attenuation map at 140 keV as shown by Hasegawa et al., for a prototype SPECT/CT detector block. Dual-energy CT is an accurate technique for determining the Compton and photoelectric contributions in these energy ranges, but the extrapolation of the monoenergetic attenuation map to 511 keV is not readily apparent. Additionally, the formation and detection of two CT spectra is technically challenging, requiring either the mechanical switching of foil filters, or the switching of the X-ray tube accelerating voltage, which is limited by the possibility of overheating. It also generally requires a complex calibration procedure.

The development of 3D PET has resulted in the acquisition of PET data with a significant fraction of scattered events. This is because the role of the septa, which are retracted during a 3D acquisition, is primarily to shield the detectors from out-of-plane scatter. The absence of shielding is reflected in a factor of three increase in scatter, from 10%-15% of the total events collected in 2D with septa extended, to 40%-45% in 3D with the septa retracted. This increase has served to focus attention on the problem of scatter correction in PET. However, even in 2D, for accurate quantitation, the scatter background of 10%-15% must be subtracted. The non-negligible scatter contribution in 2D PET comes mainly from in-plane scatter, and is a consequence of the poor energy resolution of the BGO block design. Loss of light in the block results in a decrease in energy resolution from an intrinsic 11% to as much as 23% in a block design. PET scanners are therefore operated with a lower energy threshold set typically between 250 keV and 350 keV to minimize the rejection of unscattered photons. At such a threshold, photons which lose only a small amount of energy by scattering, and are hence deviated through a small angle, are accepted as true, photopeak events. Application of an energy threshold therefore results in the preferential selection of the more forward-peaked component of the energy spectrum.

The consequence of one or both coincidence photons scattering before reaching the detector is a mispositioning of the event into a different, incorrect, LOR. However, attenuation correction in PET assumes that events have been removed from LOR's. This is accomplished either by photoelectric absorption, which is a negligible effect at 511 keV, or by Compton scattering, and not by simply being repositioned from one correct LOR to another. Therefore, the correction for mispositioning, or scatter correction, must precede correction for attenuation. Otherwise, the attenuation correction, which is an exact procedure in PET, will also be applied to the mispositioned events. This effectively distorts and amplifies the effect of scatter, making an effective scatter correction considerably more complex.

Unlike scatter in single photon tomography (SPECT), scattered events in PET may be mispositioned to LOR's outside the body. This observation has led to a simple scatter correction technique that is reasonably effective in correcting for scatter within the brain. In this approach, the distribution of the mispositioned events outside the brain is used to estimate the scatter background within the brain. While this procedure may be reasonably effective for the brain and at the low levels of scatter encountered in 2D PET, it is not satisfactory for determining scatter in other parts of the body, or in handling the increased amount of scatter in 3D. More accurate 2D scatter correction techniques have been developed by, for example, M. Bergström et al., "Correction for scattered radiation in a ring detector positron camera by integral transform of the projections," *J. Comput. Assist. Tomogr.* 7(1), 42-50 (1983); and M. Endo et al., "Software correction of scatter coincidence in positron CT," *Eur. J. Nucl. Med.* 9, 391-396 (1984), based on integral transform methods. This approach models scatter as a spatially-invariant convolution of the unscattered projection data with a kernel determined from line source or point source measurements in a uniform phantom. Since the scatter background depends on both the tracer distribution and the density distribution of the scattering medium, the convolution approach has only a limited potential to account for such spatially-variant effects.

In 3D, the increased amounts of scatter demand an accurate correction procedure to improve contrast, without losing the quantitation which is a unique feature of PET. S. R. Cherry et al., "Correction and characterization of scattered events in three dimensional PET using scanner with retractable septa," *J Nucl Med* 34, 671-678 (1993), have proposed the use of an auxiliary 2D scan from which the scatter distribution in 3D can be estimated. Following the Bergström-type approach, D. L. Bailey et al., "A convolution-subtraction scatter correction method for 3D PET," *Phys Med Biol* 39, 412-424 (1994), investigated a convolution-subtraction method to correct for scatter. The scatter kernel is modeled as a mono-exponential function of the form $k^{(-b|x|)}$, where k is the scatter ratio (scatter/trues) and b is the slope of the tails of the scatter distribution. The parameters k and b are obtained from line source measurements in an appropriate phantom (e.g. a 20 cm diameter uniform cylinder), and x is then the distance from the line source. The procedure is iterative, such that in the first step the scatter is obtained from the convolution of the measured projection data with the scatter kernel. This scatter estimate is then subtracted from the measured projections. However, this first step will tend to overcorrect because the measured projection data used in the convolution includes scatter. In subsequent iterations, the kernel is convolved with the measured projection data after subtraction of scatter estimated from the previous step. Three to four iterations are typically sufficient. A recent improvement to this method (Bailey et al.) has been the introduction of a spatially-variant scatter ratio (k(x)), based on geometrical information obtained from the PET transmission scan. This approach may therefore be improved by use of the CT scan rather than the PET transmission scan.

A second approach taken by D. Gagnon et al., "Introduction to holospectral imaging in nuclear medicine for scatter subtraction," *IEEE Trans Med Imaging* 8(3), 245-250 (1989), which has been evaluated for scatter correction in 3D PET, is based on the use of multiple energy windows, a procedure that has its origins in single photon tomography. In this approach, data is simultaneously collected in more than one energy window, and the information from other windows is used to estimate the scatter within the photopeak window. State-of-the-art PET scanners have the capability to acquire data in two energy windows, and two different implementations of a dual energy window scatter correction have been proposed. The first, studied by S. Grootoonk et al., "Correction for scatter using a dual energy window technique with a tomograph operating without septa." *IEEE 1991 Medical Imaging Conference Record,* 1569-1573 (1992), sets a lower energy window which is assumed to contain predominantly scatter. Data collected in this lower window are then scaled to provide an estimate of the scatter contribution in the photopeak window, where the scaling factors are obtained from line source measurements in air and phantoms. A second dual-energy window approach, the Estimation of Trues Method due to B. Bendriem et al., "A PET scatter correction using simultaneous acquisitions with low and high lower energy thresholds," *IEEE 1993 Medical Imaging Conference Record* 3, 1779-1783 (1994), sets an upper window with a very high (650 keV) lower threshold such that it contains only true coincidences. Again, the information in this window is used to estimate the contribution of true coincidences in the photopeak window. This approach has the advantage that the estimate in the upper window does not depend upon the scattering medium since it contains only true coincidences. Statistical noise may be a problem, however, due to the small number of counts collected in this upper window. In contrast to the convolution-subtraction method, the dual-energy window approach can in principle take into account scatter from activity outside the field-of-view, at least to the extent to which this information is contained in the lower energy window. For the method of Grootoonk et al., efforts are also being made to incorporate spatial information based on the PET transmission scan.

A third method investigated by J. M. Ollinger is to directly model the scatter using the Klein-Nishina equation describing Compton scattering. This method is disclosed in Ollinger, J. M., "Model-based scatter correction for fully 3D PET," *Phys Med Biol.* 41(1), 153-176, (1996). In this approach, the tracer distribution is obtained from a reconstruction uncorrected for scatter, and the geometry of the scattering medium is obtained from the PET transmission image. The expected distribution of scatter in the projections is then calculated using the Klein-Nishina equation which gives the probability of a photon scattering through a particular angle. Such an approach obviously involves considerable computational effort, and an efficient implementation has been developed by Ollinger which is capable of estimating the distribution of scatter in the projections within a few minutes on a fast processor. Detailed Monte Carlo simulations of scatter yield a generally low-frequency background with few features of the underlying tracer distribution or scattering medium. Therefore, it is sufficient to model such a slowly-varying distribution at a lower spatial resolution than the measured projection data, thereby considerably reducing computation time. Again, since this method has no information concerning activity outside the field-of-view, the calculated scatter distribution will not in general correct for such an eventuality. Watson et al., have independently developed a similar approach to Ollinger based on a single scatter model, as disclosed in Watson, C. C., D. Newport, and M. E. Casey, "A single scatter simulation technique for scatter correction in 3D PET" in: Grangeat P and J-L Amans, *Three Dimensional Image Reconstruction in Radiology and Nuclear Medicine.,* Dordrecht: Kluwer Academic. 255-268 (1996).

Thus, the techniques, both 2D and 3D, which have been developed to correct for scatter in PET may be summarized as (1) profile subtraction based on extrapolating the background level from outside the object; (2) integral transforms on 1D projection data; (3) estimating 3D scatter from a measurement of scatter in 2D; (4) iterative convolution-subtraction with a spatially-variant scatter fraction; (5) dual energy window, including the ETM approach; and (6) a model-based method in which the scatter contribution is calculated. Other approaches, such as the use of multiple energy windows are not possible with this scanner design. All methods for scatter correction in 3D PET have demonstrated a certain amount of success by reducing scatter to a level below that generally accepted for 2D PET. However, the accuracy of techniques described above can certainly be improved by incorporating geometrical information more precise than that currently available from a PET transmission scan.

One possibility that arises when anatomical CT data is accurately co-registered with functional PET data is to use the CT image to constrain the PET image reconstruction. A maximum a posteriori (MAP) method has been explored with co-registered PET and MR images by R. Leahy et al., "Incorporation of anatomical MR data for improved functional imaging with PET," *Information Processing in Medical Imaging*, XIIth IPMI International Conference, Wye, UK, 105-120. (1991); X. Yan et al., "MAP estimation of PET images using prior anatomical information from MR scans," IEEE 1992 *Medical Imaging Conference Record* 2, 1201-1203 (1993); and others. Promising results from simulation studies by Z. Zhou, et al., "A comparative study of the effects of using anatomical priors in PET reconstruction," *IEEE* 1993 *Medical Imaging Conference Record* 3, 1749-1753 (1994), show that incorporation of prior anatomical boundary information into the MAP reconstruction process can significantly reduce bias and noise in images. This was based on comparisons of the MAP-based reconstructions to those produced by other reconstruction methods, including filtered-back-projection and standard expectation-maximization (EM).

Traditionally, imaging modalities such as CT, MR, SPECT and PET, each with their own individual historical development, have contributed separately, but often in a complimentary way, to the overall diagnosis of pathological conditions. With the introduction of PACS (Picture Archiving and Communication Systems), routine access to image data from two or more of these modalities has become possible. The potential to combine functional and anatomical images is a powerful one and, as discussed, there has been significant progress in the development of multi-modality image co-registration and alignment techniques. However, with the exception of the brain, the re-alignment of images from different modalities is not straightforward, even when surface markers or reference points are used.

Other devices have been produced to perform two independent imaging procedures on a patient. Typical of the art is the device disclosed in the U.S. Pat. No. 6,205,347 B1, issued to H. T. Morgan et al., on Mar. 20, 2001. Morgan et al., disclose a multi-modality diagnostic imaging system including first and second imaging subsystems. These subsystems are described as being a CT system and a nuclear medicine system (NUC), namely SPECT. The first and second subsystems are provided for performing first and second imaging procedures, respectively, on a subject, and are remote from one another.

BRIEF SUMMARY OF THE INVENTION

In accordance with the teachings of the present invention, an X-ray CT and PET tomograph having a physically known relationship one with the other. Each of the X-ray CT and PET tomograph are configured for use with a single patient bed such that a patient may be placed on the bed and moved into position for either or both of an X-ray CT scan and a PET scan. This is accomplished in a first instance wherein X-ray CT detectors and PET tomograph detectors are disposed within a single gantry, and wherein a patient bed is movable therein to expose a selected region of the patent to either or both scans. In a second instance, the X-ray CT and PET tomograph detectors are disposed in separate gantries which are fixed relative to each other, and wherein the patient bed is movable between the gantries. In a third instance, the X-ray and PET tomograph detectors are disposed in separate gantries, either of which is movable with respect to the other, wherein the patient bed is movable with respect to each gantry.

The tomograph acquires functional and anatomical images which are accurately co-registered, without the use of external markers or internal landmarks. CT data is used to improve the correction of the PET data for attenuation and for contamination from scattered photons. By using the CT image in this manner, low-noise attenuation correction factors for PET are generated, and by integrating the anatomical information from the CT into scatter correction methods, an accurate scatter correction is obtained.

BRIEF DESCRIPTION OF THE SEVERAL VIEWS OF THE DRAWINGS

The above-mentioned features of the invention will become more clearly understood from the following detailed description of the invention read together with the drawings in which:

FIG. 1A illustrates a PET transmission image for a transaxial section through a patient;

FIG. 1B illustrates a CT image of the same transaxial section of FIG. 1A, showing reduced noise and increased contrast compared with the corresponding PET transmission image of FIG. 1A;

FIG. 2A is a schematic diagram of the side view of the PET/CT scanner of the present invention showing the CT scanner and PET scanner disposed within a single gantry;

FIG. 3 illustrates a display and control window for the PET/CT viewing tool of the present invention, the PET image being displayed in the right window and either the CT or fused PET/CT image in the left window;

FIG. 4A illustrates a central transaxial section of a transmission image of the thorax of a normal volunteer acquired for 3 min per bed position using dual 30 MBq germanium rod sources;

FIG. 4B illustrates the central transaxial section of a transmission image of the thorax of FIG. 4A of a normal volunteer acquired for 3 min per bed position using dual 550 MBq cesium point sources;

FIG. 8A illustrates a transaxial PET emission image of a thorax phantom using CT-based attenuation correction;

FIG. 8B illustrates a transaxial PET emission image of a thorax phantom using CT-based attenuation and scatter correction;

FIG. 9A illustrates a transverse slice through the reconstructed image (FORE+PWLS) of a torso phantom with four hot spheres and three cold spheres of different sizes with no anatomical priors;

FIG. 9B illustrates the same transverse slice of FIG. 9A with anatomical priors;

FIG. 9C illustrates the same transverse slice of FIG. 9A with blurred anatomical priors;

FIG. 10A illustrates a CT image of primary lung cancer imaged in the PET/CT scanner demonstrating a large lesion with a necrotic center in the posterior of the right lung;

FIG. 10B illustrates a PET image of the primary lung cancer imaged in FIG. 10A;

FIG. 10C illustrates a fused PET and CT image of the primary lung cancer imaged in FIG. 10A;

FIG. 11A illustrates a CT image of non-Hodgkin lymphoma imaged in the PET/CT scanner demonstrating a dorsal lesion located in the subcutaneous fat;

FIG. 11B illustrates a PET image of the non-Hodgkin lymphoma imaged in FIG. 11A;

FIG. 11C illustrates a fused PET and CT image of the non-Hodgkin lymphoma imaged in FIG. 11A;

FIG. 12A illustrates a CT image of primary pancreatic cancer imaged in the PET/CT scanner demonstrating a dorsal lesion located in the subcutaneous fat;

FIG. 12B illustrates a PET image of the primary pancreatic cancer imaged in FIG. 12A;

FIG. 12C illustrates a fused PET and CT image of the primary pancreatic cancer imaged in FIG. 12A;

FIG. 13A illustrates a CT image of a bulky right supraglotic and hypopharangeal tumor imaged in the PET/CT scanner demonstrating a dorsal lesion located in the subcutaneous fat;

FIG. 13B illustrates a PET image of the a bulky right supraglotic and hypopharangeal tumor imaged in FIG. 13A; and FIG. 13C illustrates a fused PET and CT image of the a bulky right supraglotic and hypopharangeal tumor imaged in FIG. 13A.

DETAILED DESCRIPTION OF THE INVENTION

Figure 2B:
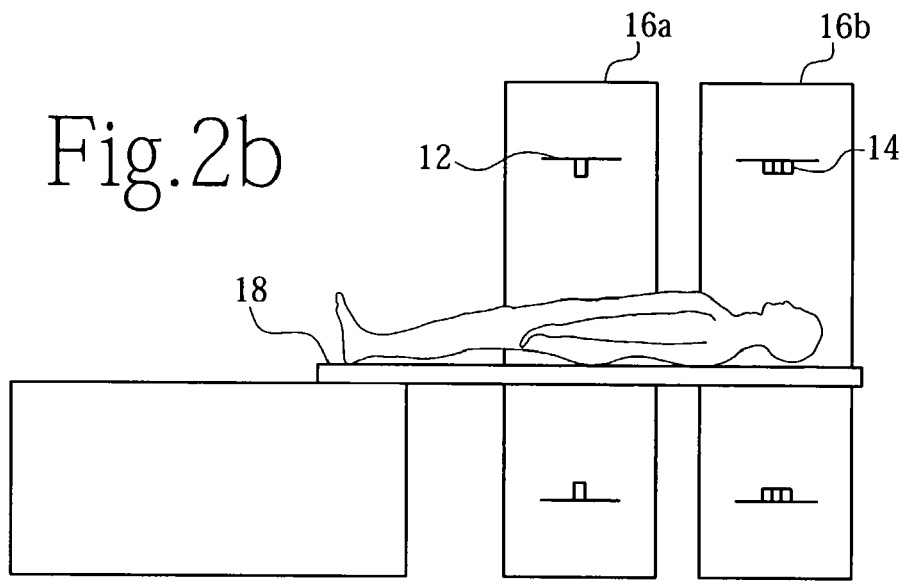
FIG. 2B illustrates an alternate embodiment wherein the X-ray CT and PET tomograph detectors are disposed in separate gantries which are fixed relative to each other and the patient bed is movable between the gantries.

A combined PET and X-Ray CT tomograph, constructed in accordance with the present invention, is illustrated generally as 10 in the figures. The combined PET and X-Ray CT tomograph, or PET/CT scanner 10 allows registered CT and PET images to be acquired sequentially in a single device, overcoming alignment problems due to internal organ movement, variations in scanner bed profile, and positioning of the patient for the scan. In order to achieve good signal-to-noise (SNR) for imaging any region of the body, an improvement to both the CT-based attenuation correction procedure and the uniformity of the noise structure in the PET emission scan is provided.

In the described embodiment, the PET/CT scanner 10 combines a Siemens Somatom AR.SP spiral CT scanner 12 with a rotating ECAT ART PET scanner 14. The PET/CT scanner 10 includes a PET scanner 14 and a CT scanner 12, both commercially-available, in a physically known relationship one with the other. Each of the X-ray CT scanner 12 and the PET scanner 14 are configured for use with a single patient bed 18 such that a patient may be placed on the bed 18 and moved into position for either or both of an X-ray CT scan and a PET scan.

In the illustrated embodiment of FIG. 2A, the completed PET/CT scanner is shown having X-ray CT detectors 12 and PET tomograph detectors 14 being disposed within a single gantry 16, and wherein a patient bed 18 is movable therein to expose a selected region of the patent to either or both scans. For testing, a Somatom AR.SP (spiral) CT scanner, manufactured by Siemens in Erlangen, Germany, and an ECAT ART PET tomograph, manufactured by CTI PET Systems (Knoxville, Tenn., USA) and distributed through Siemens, were used. The two systems are combined by mounting the ECAT ART components onto the rear of the AR.SP on a common rotating support.

Figure 2C:
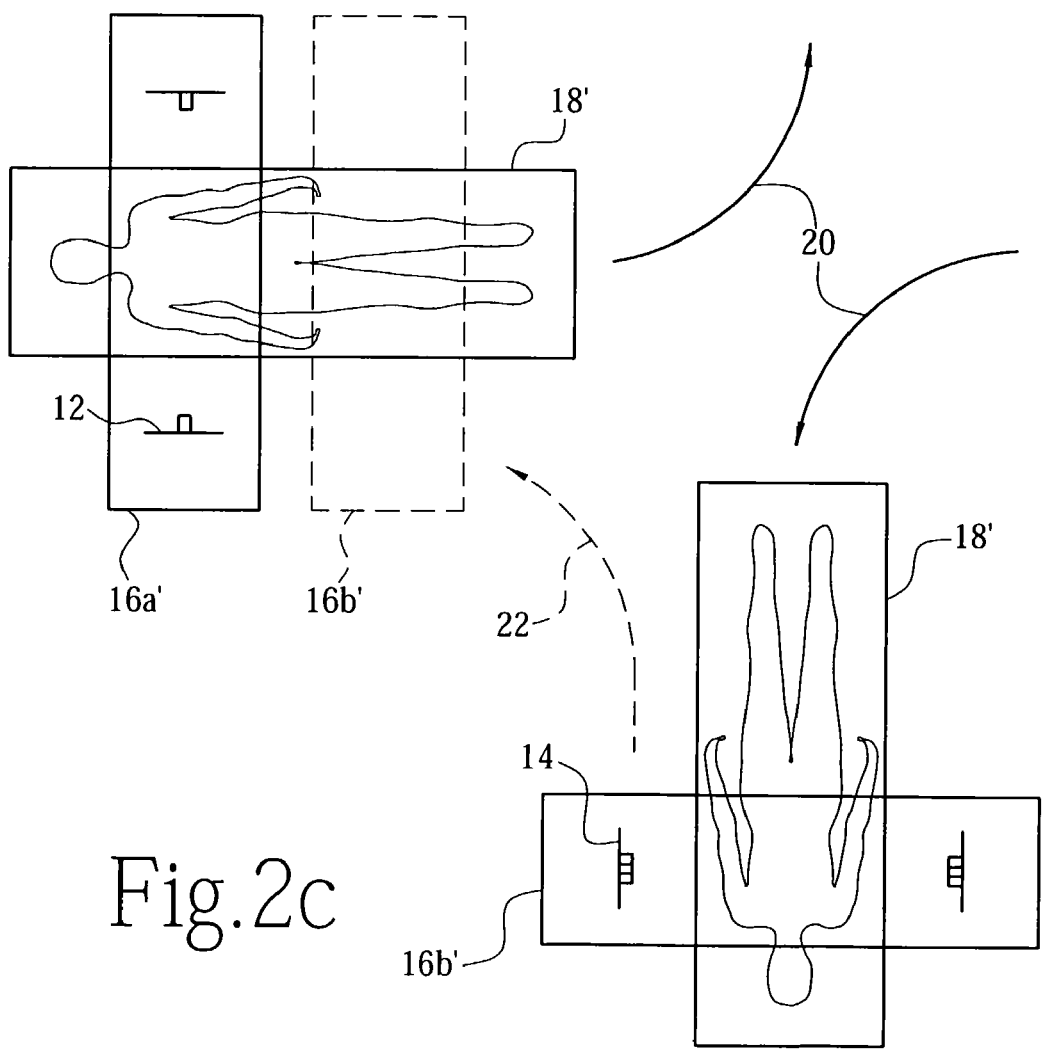
FIG. 2C illustrates a further alternate embodiment wherein the X-ray and PET tomograph detectors are disposed in separate gantries, either of which is movable with respect to the other, and wherein the patient bed is movable with respect to each gantry.

In a second instance, illustrated in FIG. 2B, the X-ray CT and PET tomograph detectors 12,14 are disposed in separate gantries 16A,B which are fixed relative to each other, and wherein the patient bed 18 is movable between the gantries 16A,B. In a third instance, illustrated in FIG. 2C, the X-ray and PET tomograph detectors 12,14 are disposed in separate gantries 16A',B', either of which is movable with respect to the other, wherein the patient bed 18' is movable with respect to each gantry 16A',B', as indicated by the arrows 20. Alternatively, one or both gantries 16A',B' may be moved relative to the patient bed 18' and the other of the gantries 16A',B' as indicated by the arrow 22. In each of these embodiments as illustrated in FIGS. 2A-2C, it is shown that the patient is placed on a single patient bed 18 for either or both scans, with either or all of the scanning devices and the patient bed is/are moved to accomplish the required scan(s).

The PET/CT scanner of the illustrated embodiment rotates at 30 rpm and is housed within a single gantry with dimensions of 168 cm high and 170 cm wide. The patient entry port defines a diameter of 60 cm and a tunnel length of 110 cm. The CT aperture is at the front of the scanner and the PET imaging volume is at the rear. The center of the PET volume is displaced 60 cm axially from the center of the CT slice. A set of contiguous spiral CT scans of a whole-body is acquired in two to three minutes as the patient bed moves continuously through the scanner. The PET scan is acquired in multi-bed mode with data acquisition lasting up to ten minutes at each bed position. Depending on the number of bed positions required to cover the region to be scanned, the complete PET scan may take forty to fifty (40-50) minutes, in addition to the forty-five to sixty (45-60) minute uptake period. The PET/CT scanner of this embodiment has the capability to scan a combined axial length of up to 100 cm by both modalities. While specific dimensions and lengths are described herein, it will be understood that these dimensions are for illustration purposes only and are not intended as limitations of the present invention.

The CT scan is acquired before the PET scan, following a sixty (60) minute uptake period after $^{18}$F-FDG activity has been injected into the patient. No degradation of the CT image is observed due to the activity in the patient. The CT images are reconstructed on the CT acquisition computer and then transferred to the PET console. The CT images are used to generate the attenuation correction factors. Specifically, the attenuation image at 511 keV is estimated by first using a threshold to separate out the bone component of the CT image, and then using separate scaling factors for the bone and non-bone component. These factors are applied after scatter correction to the PET emission data to correct for attenuation, and the PET images are then reconstructed using a Fourier rebinning technique (FORE) and then independently by the ordered-subset EM (OSEM) iterative reconstruction algorithm (FORE+OSEM).

To this extent, significant progress has been made in improving PET image quality through the use of statistically-based reconstruction algorithms. These improvements are particularly significant for count-limited, whole-body PET scanning where statistically-based algorithms such as FORE+OSEM offer substantially improved image quality compared to the standard 3D reprojection method (3DRP). These algorithmic developments are also important for the PET/CT scanner due to the high noise level in the low-count emission scan.

The FORE technique accurately and noiselessly rebins 3D PET data into a 2D data set, thus enabling a 2D iterative reconstruction algorithm to be applied to a rebinned, fully 3D data set. The resulting 2D sinograms from FORE are reconstructed independently by the ordered-subset EM (OSEM) iterative reconstruction algorithm. The PET pixel values are scaled to Standardized Uptake. Values (SUVs) according to the usual expression:

$$SUV = \frac{ROI \text{ counts(MBq/ml)}}{\{\text{Injected dose(MBq)}\}/\{\text{body weight(g)}\}}$$

where the scanner has been calibrated to yield tissue concentration in the tumor ROI in absolute units of radioactive concentration (MBq/ml). The expression may be modified to use the lean body weight to account for the uptake of $^{18}$F-FDG primarily into muscle rather than fat. SUV has been used to distinguish significant uptake in malignant tissue from uptake in a normal or non-malignant process by adopting a threshold—an SUV greater than a particular value (e.g. 2.5) is suggestive of a malignant process. Glucose level, time after injection, ROI size and scanner resolution are fixed when performed on the PET/CT. Plasma glucose levels are checked by obtaining a 1 ml blood sample at the end of the patient scan.

The images are displayed with the PET adjacent to the corresponding CT sections, and also as fused PET and CT images. The display tool allows the physicians reading the images to scan through the volume, viewing either the fused images or the PET and CT images separately with a linked cursor. The PET images are scaled in SUV values.

The PET images are therefore fully quantitative and are interpolated and displayed with the same pixel size as the CT images. PET images are displayed either adjacent to, or superimposed on, CT images for simultaneous interpretation of functional and morphological information. In one embodiment, the PET and CT images are displayed side by side in a viewing tool with linked cross-hair cursors, so that positional correspondence between the two image sets is easily established. A second technique of image 'fusion' is also employed, where the two different image sets are combined into a single image. See FIG. 3. For display of the fused PET and CT images, an alternating pixel method is extended to a 3D display format. Since the PET images have an isotropic resolution of approximately 10 mm for whole-body oncology imaging, the images are interpolated into the CT image space without loss of information in the PET image, thus preserving the resolution of the CT image. Because image fusion methods can obscure low-contrast objects, the CT display panel can be toggled between CT only and fused PET/CT mode. The viewing panels also have independent color scales and can be switched between transverse, sagittal, and coronal viewing modes.

The fused image display offers a two-dimensional, slice-by-slice approach to the display of a three-dimensional volume data set. In order to offer a fully 3D approach to the data, and enhance the display capabilities of the PET/CT, a 3D display computer is added to the CT scanner. The 3D display computer offers interactive 3D shaded graphics of anatomical structures, displayed as shaded surfaces with or without transparency. The addition of functional structures, such as tumor masses, to the 3D anatomical framework has considerable diagnostic utility, with the 3D display computer providing the user with the ability to explore the functional anatomy of the human body fully in three dimensions.

The CT scanner used for testing in the combined PET/CT design is a third generation spiral, or helical, CT tomograph. A number of design parameters of the Somatom AR.SP are as follows:

| | |
|---|---|
| Tube voltage [kV$_P$]: | 110, 130 |
| Tube current [mA]: | 63, 83, 105 |
| Scan time per slice [s]: | 1.3, 1.9 (multiple cycles possible) |
| Slice thickness [mm]: | 1, 2, 3, 5, 10 |
| Gantry aperture [mm]: | 600 |
| Transaxial FOV [mm]: | 450 |
| Fan beam opening [deg]: | 52.2 |

The AR.SP used has a metal ring M-CT 141 tube that produces X-ray spectra of 110 kV$_P$ and 130 kV$_P$ with a 6.5 mm Al-equivalent filter. The tube is operated with a flying spot, which doubles the number of detector position readouts to 1024 from 512 xenon gas-filled Quantillarc detector chambers. The X-ray tube, detectors and most of the data processing system of the CT are mounted on the rotating support driven by a synchronous motor.

The standard ECAT ART (PET) scanner comprises dual arrays of BGO block detectors. Each array consists of 11 blocks disposed in a transaxial direction by 3 blocks disposed axially, covering an arc of approximately 83°. The detector arrays are not symmetrically opposed but are offset by approximately 15° so as to increase the diameter of the transaxial FOV to 60 cm without requiring additional detector blocks. The ART has 46% of the detectors in the corresponding stationary, full-ring scanner, the ECAT EXACT. The detector blocks are approximately 54 mm×54 mm×20 mm in size, cut into 8×8 crystals each dimensioned to approximately 6.75 mm×6.75 mm×20 mm. The 8×8 crystal array is viewed by four photomultiplier tubes and Anger-type logic is used to localize the photon interactions within the block. The axial FOV is 16.2 cm, subdivided into 24 partial rings of detectors. Shielding from out-of-field activity is provided by arcs of lead, approximately 2.5 cm thick, mounted on both sides of the detector assembly and projecting approximately 8.5 cm into the FOV beyond the front face of the detectors.

The ECAT ART scanner has no septa and the detector arrays and shielding rotate continuously at 30 rpm to collect the full set of 3D projections required for image reconstruction. A complete 3D data set is acquired every two seconds. Continuous rotation eliminates the requirement for additional gantry cooling, and fans start automatically if, for any reason, gantry rotation is halted. An encoder monitors the position of the gantry during rotation, so that the acquired LOR's are assigned to the correct sinogram addresses. Power and serial communications to the rotating assembly are transmitted over mechanical slip rings, while high speed digital data transfer is by optical transmission.

In the standard ART scanner configuration, attenuation correction factors are obtained from a transmission scan performed with two rotating rod sources mounted at opposite ends of one detector array. In the PET/CT scanner of the present invention, dual 550 MBq $^{137}$CS collimated point sources are used to provide significantly improved transmission image quality with reduced scan duration. Using the cesium point sources, an additional approximately three (3) minutes per bed position is required for the transmission scan. The cesium singles sources provide an alternative to CT-based attenuation correction, and the combined PET/CT scanner has the capability of being operated in PET or CT mode independently, and can also acquire both types of transmission image allowing for a comparison to be made between the two approaches.

Through testing, the performance characteristics of the combined PET and CT components have been verified to be identical to the performance of each device separately. The performance of the ECAT ART has been assessed according to the NEMA protocol and has been found to be in agreement with published data.

Standard performance measurements for CT scanners include the determination of attenuation values of air and water, in addition to image pixel noise and spatial resolution. Attenuation values for water were measured using the test protocol of the Somatom AR.SP. A 20 cm diameter water-filled cylinder was placed in the center of the transaxial FOV and tomograms were acquired at 110 kV$_P$ and 130 kV. Mean pixel value and standard deviation were calculated from a circular region-of-interest (ROI) covering 80% of the area of the water phantom. A similar measurement was performed with no object placed inside the FOV to determine the attenuation value of air. The values for air and water are defined to be −1000 HU and 0 HU, respectively, and should be independent of the X-ray tube voltage. Mean CT numbers were also determined from five circular ROI's, 4 cm in diameter, including a central ROI and four equally spaced peripheral ROI's. The absolute value of the difference between the average CT numbers of the central test ROI and the CT numbers of the four peripheral ROI's represents the homogeneity at 110 kV$_P$ and 130 kV$_P$, respectively. The spatial resolution is determined by scanning an air-filled cylinder with a thin metal wire positioned parallel to the main scanner axis. The resolution is expressed in line pairs per cm. The results of these measurements for the CT components are summarized as follows:

| | |
|---|---|
| Transaxial spatial resolution [mm] | 0.45 (at 1.9 s scan time) |
| CT value of air [HU] | −1002 ± 10 |
| CT value of water [HU] | −2 ± 4 |
| Cross-field uniformity [HU] | <0.5 (with 20 cm water filled cylinder) |
| Contrast scale (factory value) | $(1.90 ± 0.03) \cdot 10^{-4}$ |
| Contrast resolution (factory value) | 2.5 mm/5 HU/1.9 s |

No significant degradation of the performance of either the ECAT ART or the Somatom AR.SP was identified as a consequence of having the two devices mounted in the same gantry. Because the performance of BGO PET detectors is temperature-dependent, the PET/CT scanner was tested for potential temperature fluctuations inside the PET/CT gantry, and specifically for increases due to the operation of, and heat dissipated by, the X-ray tube. The temperature inside the gantry was measured during the CT operation and an increase of only 1° C. was observed, too small to significantly affect the performance of the ART scanner. Results of the testing showed that the PET and CT components may be operated independently with identical performance to the standard Somatom and ECAT ART.

The effect of photon attenuation in the PET/CT scanner is corrected through the use of attenuation correction based on the CT images. In so doing, there is no emission contamination in post-injection CT transmission scans, lower statistical noise of the CT data compared to a standard PET transmission scan, and elimination of the cost of the periodic replacement of transmission sources. However, an accurate scaling algorithm is required to transform the attenuation factors from the CT energies (typically 40-140 keV) to 511 keV, as disclosed by Kinahan, P. E., D. W. Townsend, T. Beyer, and D. Sashin. "Attenuation correction for a combined 3D PET/CT scanner," *Med Phys* 25(10), 2046-2053 (1998).

The PET/CT scanner is equipped with dual, collimated, cesium sources, each with an activity of 550 MBq. The point sources move in the axial direction to scan the full field-of-view. The collimators reduce the contribution from scattered photons. The high activity level of the cesium sources compared to the germanium rods results in a significant improvement in transmission image quality. This improvement is shown in FIGS. 4A and 4B for a transmission scan of the thorax of a normal volunteer. The scan duration of three (3) minutes was the same for both acquisitions. The superior image quality of the singles acquisition is evident from FIG. 4B, thus illustrating the comparison of an emission scan reconstructed with attenuation correction factors obtained from a point source transmission scan with the same emission scan reconstructed with CT-based attenuation correction factors, as will be described in further detail below.

A hybrid scaling method is used for CT-based attenuation correction. This hybrid scaling method is based on the principal that, over the photon energy range covering both CT and PET (40 to 511 keV). Compton scattering is the most important physical process for the interaction of photons with matter such as air, water, and soft tissue. For these substances, the mass attenuation coefficient, determined by the linear attenuation coefficient divided by density, is almost the same at each photon energy, and thus the relative change in linear attenuation coefficient between two photon energies is essentially the same. The X-ray beam is polychromatic. Therefore, for the X-ray source in the Somatom, an energy of 70 keV represents a reasonable mean value for an effective beam energy. The change in linear attenuation coefficient from a mean CT energy of 70 keV to the PET energy of 511 keV is approximately 0.53 for air, fat, water, blood, soft tissue, muscle, and lungs. The same scaling factor does not, however, apply to bone because the photoelectric cross-section at CT energies is significantly increased due to the relative abundance of calcium in bone. A separate scaling factor must therefore be introduced for bone and other highly attenuating structures. At 511 keV, the contribution from the photoelectric effect is essentially negligible. All photon interaction in biological tissues, including bone, is dominated by Compton scattering.

Figure 5A:
FIG. 5A illustrates the CT image of a transverse image section prior to CT-based attenuation correction for a typical clinical PET/CT study.
Figure 5B:
FIG. 5B illustrates the scaled attenuation map of the CT image of FIG. 5A calculated using the hybrid segmentation and scaling method and smoothed to match the resolution of the PET data.
Figure 5C:
FIG. 5C illustrates the attenuation-corrected PET emission image of the CT image of FIG. 5A.

The CT images are scaled from 70 keV to 511 keV in three steps (Kinahan et al., 1998). First, the CT image is divided into regions of pixels classified as either non-bone or bone by simple thresholding or more sophisticated segmentation methods. A threshold of 300 Hounsfield units (HU) gives acceptable results. Non-bone classified pixel values are then scaled with a single factor of 0.53, and bone classified pixel values are scaled with a lower scaling factor of 0.44. Finally, attenuation correction factors along oblique LOR's are obtained by forward projection through the segmented and scaled CT images. An illustrative example is shown in FIGS. 5A, 5B and 5C. The original CT image is shown in FIG. 5A, and the corresponding image after segmentation and scaling to 511 keV is shown in FIG. 5B. These figures illustrate the considerable detail that is preserved at the higher energy after scaling. Such detail is generally not visible on PET transmission images, illustrated in FIG. 5C, owing to the high level of statistical noise, even with cesium transmission sources.

Figure 6A:
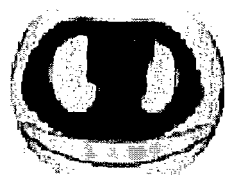
FIG. 6A illustrates the transmission images of a transverse section through a whole-body phantom acquired using the CT scanner.
Figure 6B:
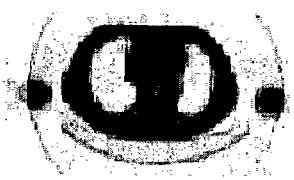
FIG. 6B illustrates the transmission images of the same transverse section of FIG. 6A through a whole-body phantom acquired using the cesium sources in singles mode.

The PET/CT scanner of the present invention, providing both a CT scan and a standard PET transmission scan with cesium sources, allows the two approaches to be compared, and the CT-based attenuation correction algorithm to be evaluated in patients. To illustrate such a comparison, FIG. 6A shows the CT image of a transverse section through a whole-body phantom with arms in the field-of-view, and FIG. 6B shows the corresponding transmission image of the same section obtained with the cesium sources.

As with patient studies, the arms are truncated on the CT scan owing to the smaller, 45 cm diameter, transaxial field-of-view of the scanner. For this simple phantom, the two images are comparable except for the truncation of the arms on the CT scan (FIG. 6A), and the increased statistical noise from the cesium transmission sources (FIG. 6B). The increase in noise is a result of the photon flux from the X-ray source, which is equivalent to an activity of $2\times10^8$ MBq, compared to only 550 MBq in each of the cesium sources. The average µ-value for a region-of-interest 10 cm×2 cm in size in the "mediastinum" of the phantom is $0.097\pm0.0003$ cm$^{-1}$ and $0.095\pm0.007$ cm$^{-1}$ for the CT and the cesium source scan, respectively.

Figure 7A:
FIG. 7A illustrates the emission image corresponding to the transmission images of FIG. 6A, reconstructed using CT-based attenuation correction factors.
Figure 7B:
FIG. 7B illustrates the emission image corresponding to the transmission images of FIG. 6B, reconstructed using standard singles-based PET attenuation correction factors.

FIGS. 7A and 7B illustrate the corresponding emission scans reconstructed with CT-based attenuation correction, and the standard PET attenuation correction with the cesium sources, respectively. The two reconstructed emission images are similar, except for the presence of the arms in FIG. 7B. This is due to the larger transaxial field-of-view (FOV) of the cesium source transmission scan that matches the 60 cm diameter FOV of the PET emission scan. An ROI placed on the "mediastinum" of the reconstructed emission image has a mean value (in arbitrary units) of $8.9\pm1.2$ and $8.5\pm1.4$ for the CT-based (FIG. 6A) and cesium source-based (FIG. 6B) attenuation correction factors, respectively. The similarity of the variances on these means indicates that the dominant contribution to the noise in the study illustrated in FIGS. 7A and 7B originates from the photon statistics (noise) in the emission scan and not from the transmission scan.

Scatter correction for the PET emission scans is accomplished using a single scatter simulation algorithm which estimates the scatter contribution at any point in an emission projection view by integration of a scattering kernel over the volume of the scattering medium. The scattering medium is estimated from the PET transmission scan. This scatter correction model provides routine scatter correction of combined PET/CT studies by estimating the geometry and distribution of the scattering medium from the scaled CT image. FIGS. 8A and 8B illustrate the results of CT-based scatter correction for a thorax phantom study with hot and cold lesions simulated with spheres. CT-based attenuation correction was applied as described above. Compared to FIG. 8A, FIG. 8B shows that the CT-based scatter correction significantly reduces the scatter contribution in the cold lung region and improves the contrast in the cold spherical lesion positioned between the lungs, as illustrated by the arrow.

In a further method for reconstructing PET images, Fourier rebinned PET data are reconstructed by minimizing a penalized weighted least-squares (PWLS) objective function, as disclosed by Fessler, J. A., "Penalized Weighted Least-Squares Image Reconstruction for Positron Emission Tomography," *IEEE Trans Med Imaging*, 13, 290-300 (1994). The penalty term of the objective function is a quadratic roughness penalty based on a 3D pixel neighborhood N, consisting of 26 adjacent neighbors. The penalty weights are derived from the anatomical (CT) data using voxel labels corresponding to the classification of the voxel. The weights are chosen to encourage smoothness inside, but not across, anatomical regions. For simplicity, the penalty weights are kept constant during reconstruction with FORE+PWLS, as shown by Comtat C., P. E. Kinahan, J. A. Fessler, T. Beyer, D. W. Townsend, M. Defrise, and C. Michel, "Reconstruction of 3D whole-body PET data using blurred anatomical labels," *IEEE Medical Imaging Conference Record*, CD-ROM (1999). Since in practice, mismatches between anatomical and functional data are unavoidable, the labels are "blurred" to reflect the uncertainty associated with the anatomical information. The images in FIGS. 9A, 9B and 9C illustrate the advantage of using CT-derived anatomical information in the PET image reconstruction. The contrast of the small lesion in the upper 'mediastinal' region (arrowed), in particular, is significantly improved with the use of anatomical priors, as illustrated in FIG. 9B as compared to FIG. 9A. When the anatomical labels are blurred with a 5 mm (FWHM) smoothing kernel to reflect the alignment uncertainty between the functional and anatomical images, as illustrated in FIG. 9C, the loss of lesion contrast compared to the aligned images illustrated in FIG. 9B is evident.

A wide range of applications of FDG PET for imaging cancer have been identified. The PET/CT scanner of the present invention is of particular utility in the thorax and abdomen due to the difficulty of aligning PET and CT images (with the exception of the brain) that are acquired on separate scanners, and because of the frequent difficulty of interpreting $^{18}$F-FDG PET studies in the abdomen. To date, over 65 cancer patients have been imaged on the PET/CT scanner according to the protocol described herein. Below are four illustrative case reports of lung cancer, lymphoma, pancreatic cancer and head and neck cancer. All PET images were corrected with CT-based attenuation correction, as described above, and reconstructed with FORE+OSEM, also as described above. In each case, PET imaging was performed sixty (60) minutes after an injection of 260 MBq of $^{18}$F-FDG. The PET scan duration varied depending on the study. The parameters for the spiral CT scans followed accepted protocols and were acquired with 10 mm sections, 200 mAs, 130 kV$_P$ and a pitch of 1.5. All CT scans presented herein were acquired without the administration of contrast agent.

A 72 year-old woman with primary squamous cell lung cancer was imaged on the PET/CT scanner. The PET emission scan was acquired for eight (8) minutes. The images shown in FIGS. 10A-C demonstrate a large lesion in the upper quadrant of the right lung. Although the lesion appears as a uniformly-attenuating, isodense mass on CT (FIG. 10A), the PET scan (FIG. 10B) reveals heterogeneous uptake consistent with a necrotic center and a rim of intense uptake representing high metabolic activity. The fused image (FIG. 10C) shows excellent alignment despite small differences due respiratory motion.

A 48 year-old woman with a history of non-Hodgkin's lymphoma was referred for a PET/CT scan. Spiral CT data were acquired over a limited whole-body range that extended from the upper part of the liver to the uterus. PET data were acquired at three contiguous bed positions for a scan duration of thirteen (13) minutes at each bed position. An area of pronounced $^{18}$F-FDG uptake, located dorsally at the level of the lower abdomen, was seen on the PET images (FIG. 11B). Alignment with CT images demonstrated that the increased $^{18}$F-FDG uptake corresponded to a metastasis in the subcutaneous fat (FIG. 11C). The PET scan also demonstrated $^{18}$F-FDG accumulation in the pelvic region (not shown), distinct from normal bowel activity. The fused PET/CT image localized this focal $^{18}$F-FDG uptake to a known SI bone lesion seen on the CT. Due to the large cross-sectional area of the patient, there was significant CT beam hardening, as is apparent in the dorsal region in FIG. 11A.

A 38 year-old woman with confirmed pancreatic cancer was evaluated following placement of a biliary stent. An independently acquired contrast-enhanced CT scan revealed the presence of a large, 5 cm×3 cm, hypodense pancreatic mass. The PET scan was acquired for ten (10) minutes, and revealed a region of focally-increased uptake in the head of the pancreas (FIG. 12B) with an SUV of 5.3. The location of the increased uptake was consistent with the hypodense mass seen on CT (FIG. 12C). In addition to the focal uptake in the pancreas, the whole-body PET/CT scan also revealed focally-increased $^{18}$F-FDG uptake in a right dorsal rib and in a mediastinal lymph node (not shown) suggesting spread of the disease.

Finally, a 72 year-old woman was referred for PET evaluation of a bulky supraglotic and hypopharangeal tumor, partially restricting the trachea, as illustrated in FIG. 13A. The PET scan was acquired for ten (10) minutes, and demonstrated intense uptake of FDG in the tumor with an SUV of over 30 (FIG. 13B). In addition, significant uptake was also seen in a soft tissue mass in the upper right neck and in a mass in the left neck adjacent to the jugular vein (not shown). The fused sagittal image of FIG. 13C, localizes the intense FDG uptake to the hypopharangeal mass.

The clinical studies illustrated in FIGS. 10-13 clearly illustrate the advantages and some of the challenges of the combined PET/CT scanner. A clinical analysis of the first 32 patients studied on the combined PET/CT has been completed and significant advantages of combined imaging are documented in distinguishing normal physiological uptake from possible malignancy, and in providing precise localization of lesions for subsequent surgical or biopsy procedures.

CT-based attenuation correction provides almost noiseless correction factors. However, a number of aspects have emerged in which CT-based attenuation correction requires significant improvement. These include accounting for the effects of respiratory motion, truncation of the CT field-of-view, beam hardening, and intravenous contrast agents. In the present invention, validation of the CT-based correction is performed by comparing emission scans reconstructed with CT-based factors to emission images reconstructed with factors obtained from standard PET transmission scans. For this purpose, the PET/CT scanner 10 is equipped with collimated cesium point sources operating in singles mode. Further improvement in SNR is also achieved by implementing continuous bed motion acquisition for the PET emission scan. Such an approach obviates the need to acquire overlapping bed positions that lead to axially varying SNR and lower overall efficiency. A feature of continuous bed motion is the use of list mode data acquisition, which also allows direct correction for patient movement during the scan.

The PET/CT scanner 10 is provided for the operation of a combined PET and CT scanner to perform anatomical (CT) and functional (PET) imaging in patients. The unique design is primarily targeted at whole-body oncology imaging in the thorax and abdomen with the conventional PET tracer 2-deoxy-2-($^{18}$F)-fluoro-D-glucose ($^{18}$F-FDG). The combination of both functional and anatomical images, accurately aligned, obtained in a single scanner is a powerful diagnostic tool. All specific aims from the previous proposal have been achieved.

One function of the present invention is to generate attenuation correction factors for the PET data using the co-registered CT images. In the standard ECAT ART scanner, a transmission scan is performed using dual rotating $^{68}$Ge/$^{68}$Ga rod sources in coincidence mode or, more recently using $^{137}$Cs point sources with transmission data acquired in singles mode. A single photon emitter rather than a positron emitter can be used for transmission scanning because knowledge of the source position and the detection point of the transmitted photon on the opposing detector array provide the two points that are required to define a line-of-response. The detectors close to the point source are not used, and consequently the singles source can have higher activity than coincidence sources without creating a deadtime problem for the adjacent detectors. $^{137}$Cs with an emission energy of 662 keV and a half-life of 30 years has been used as a transmission source. The energy difference between 511 keV and 662 keV is corrected by scaling the measured attenuation factors. However, a recognized problem with singles transmission measurement is the high level of scatter in the transmission data, which can be limited in the case of coincidence imaging by the use of septa and rod windowing. To reduce scatter, the use of high activity collimated point sources has been implemented for transmission measurements on the ART. The collimators limit the acceptance of wide-angle scatters, similar to the septa shielding the detectors in a full-ring tomograph.

Compared to the rotating rod and point sources, CT-based attenuation correction has a number of important advantages. Namely, CT transmission scans that are acquired after the injection of the PET tracer will not be contaminated by 511 keV photons emitted from the tracer, due to the much higher photon flux from the X-ray source and the low detection efficiency of the CT detectors at 511 keV. Post-injection transmission scans are desirable in clinical settings as they increase both patient comfort and scanner throughput. Further, the CT data have much lower statistical noise than a standard PET transmission scan, thus reducing noise in the final attenuation-corrected PET emission image, that is especially important for whole-body PET imaging. In addition, the shorter times required for the collection of the CT transmission data allow longer times for the acquisition of the PET emission scan, thus lowering statistical noise even further for a given total scan duration. Still further, it is no longer essential to include standard PET transmission sources, thus eliminating the cost both of including these components and the periodic replacement of $^{68}$Ge/$^{68}$Ga rod sources. However, the prototype PET/CT scanner incorporates cesium sources to allow the PET and CT scanners to be operated independently. The availability of both the CT scanner and singles cesium sources also allows the CT-based attenuation correction algorithm to be compared directly with a standard PET attenuation correction based on a singles source transmission scan.

Although the combined scanner achieves the best possible overall coregistration between PET and CT, in regions such as the thorax, respiration and cardiac motion may result in some intrinsic misalignment. On the CT scan, lung boundaries and regions of either high or low attenuation are susceptible to motion artifacts. With the introduction of spiral CT, such as that used in the PET/CT scanner, motion artifacts are limited almost exclusively to the lingula and the lower lung segments in close contact with the left ventricle. The shorter scan times possible with spiral CT have essentially eliminated artifacts from cardiovascular motion. The spiral CT is acquired at breath hold, with the lungs inflated. The ungated PET image, on the other hand, represents an average over the scan duration of typically 5-10 minutes. During the scan, the patient breathes normally and the resulting PET image is an integration over the respiratory and cardiac cycles. The motion of the heart and chest wall results in reduced image spatial resolution. Exact CT and PET alignment of detailed structures in the anterior of the thorax is therefore not possible. It is important to avoid systematic effects. For example, the movement of the chest wall may be suppressed by breath holding during the CT scan, and hence there is a mismatch between the anterior wall position on CT and on PET. As a result of the movement of the chest wall, incorrect ACF's are generated by the algorithm, which could result in a reduction in $^{18}$F-FDG uptake in the anterior chest wall.

CT scanners are designed with a transaxial field-of-view (FOV) of less than 50 cm diameter, a measure assuming the imaging of the thorax and abdomen is performed without the arms in the FOV. PET scanners for whole-body imaging typically have a transaxial FOV of 60 cm to allow the patient to be imaged with the arms in the FOV. This is because a whole-body PET scan may last 45-60 min, generally too long for a patient to remain comfortable with the arms above the head. The CT scan acquired with the arms in the field of view may therefore be truncated. This truncation results in artifacts at the edge of the field-of-view, and a small quantitative inaccuracy of about 10 HU maximum at the center of the field-of-view. The attenuation correction factors generated from the truncated CT image are therefore to some extent biased, affecting all reconstructed pixel values.

The region truncated is generally across the arms. The average linear attenuation coefficient for the cross section of an arm, which is primarily composed of tissue and a small amount of bone, is used to fill in the boundaries as determined from a PET image reconstructed without attenuation correction, which is never truncated owing to the larger, 60 cm, FOV of the PET scanner. A good estimate of the outer skin surface is obtained from a FORE+OSEM reconstruction due to the statistical noise reduction outside the body surface (see FIGS. 7A,B). This estimate is made more robust, when necessary, by fitting a smooth 3D surface to the exterior of the skin layer as determined from the attenuated PET image. By comparing the outline of the body as determined from the CT and attenuated PET images, the missing volume is estimated. This volume is then added to the CT image and set to the average linear attenuation coefficient for the arm.

The CT data are not truncated in the lateral views of the patient where the body cross-section is narrower. The CT sinogram data is used to directly estimate the CT attenuation for these views and scaled to the PET attenuation values. This removes some of the bias in the estimate of the non-attenuated PET emission data.

It is known that image reconstruction with missing data of an arbitrary object is insoluble, but constraints on the image or sinogram data can make the problem more tractable. The missing region in the CT image is estimated by iterative reconstruction using the additional information described above to constrain the solution. Namely, the average value data (average attenuation for the arm), the boundary data, and additional original line integral data from non-truncated CT views are used for CT image reconstruction. This information is used with a variety of iterative image reconstruction methods that operate in either image space or sinogram space. In contrast to CT-based attenuation correction, the present invention uses the PET data for additional information when reconstructing the CT image.

In order to scale the CT attenuation image from X-ray beam energies to 511 keV, a mean value for the energy of the X-ray beam is assumed. For the purposes of the hybrid algorithm, the polychromatic energy spectrum of a typical X-ray source of 140 kV$_P$ can be approximated by an average value of 70 keV. However, as is well known, the spectrum is modified by the effect of beam hardening, in which lower energy (soft) X-ray photons are preferentially attenuated by the patient, causing the mean photon energy in the beam to increase (harden) with increasing distance from the X-ray source.

Beam hardening results in a non-linear relationship between attenuation and the projection data. Such non-linearity requires an iterative approach to recover accurate attenuation values from projection data. A widely-used alternative method is to obtain suitable correction coefficients from look-up tables. Although in many imaging situations, beam hardening is satisfactorily corrected, for large patients the effect may be significant. The presence of arms in the FOV enhances the effect further, and standard beam hardening correction procedures are inadequate. The scaling of incorrect CT values to 511 keV results in biased attenuation correction factors that are then applied to the PET data. The effect is most problematic in the abdomen where maximum attenuation occurs.

The most widely-used study in $^{18}$F-FDG PET oncology is the whole-body scan. The patient is typically surveyed from head to upper thigh to identify localized regions of abnormal tracer uptake consistent with possible metastatic disease. To perform the scan, the patient bed is moved through the scanner in a sequence of discrete, overlapping steps. Data is acquired with the bed stationary, the PET scanner covering an axial extent of about 15 cm in each position. A total axial length of 80-100 cm is covered in 6-8 bed positions, with an overlap between bed positions varying from a few millimeters in 2D studies, up to 4 cm in 3D studies. The data for each bed position are acquired and reconstructed independently, and when all sets are complete, the data are assembled into a single whole body volume taking into account the overlap between each multi-bed position. Coronal and sagittal views and weighted projection images can be displayed in addition to the usual transverse sections.

The PET scanner used in the combined PET/CT device, the ECAT ART, acquires data fully in 3D. The axial sensitivity profile in three dimensions peaks in the center, resulting in highly non-uniform noise properties in the coronal and sagittal sections. To compensate for the non-uniform noise structure, a step of 12 cm is used with a 16 cm axial FOV, resulting in a 4 cm overlap at each end. In order to improve image quality in whole-body scans and to characterize the axial sampling schemes that lead to an optimal signal-to-noise (SNR) the bed is continually moved in an axial motion. The advantages of true continuous axial sampling include uniform axial SNR (except at the ends of the FOV), elimination of resolution artifacts due to axial undersampling, a reduction in the statistical noise contributed by the detector normalization factors, and a reduced sensitivity to small patient movements. Continuous axial sampling results in all detector rings acquiring data for every transaxial slice, eliminating normalization effects between detector rings. The continuously-acquired data is rebinned into finer axial sampling than the detector ring spacing, considerably reducing the aliasing artifacts due to axial undersampling arising with the multi-bed approach. The major advantage, especially for 3D data acquisition, is a more uniform SNR, eliminating the periodic variation in noise texture that may affect detectability. Continuous bed motion also results in more efficient use of the data because it avoids discarding the end planes of each bed position.

In order to implement finer axial sampling than the width of a detector ring with currently-available hardware, each LOR is acquired and stored separately in a list mode data stream and subsequently rebinned using a version of the FORE algorithm described above. A substantial increase in histogramming memory would be required to collect a full set of sinograms at finer axial sampling. The position of the bed at any moment can be read and integrated into the list mode data stream for use by the rebinning process. An additional advantage of list mode acquisition is that, if patient movement is monitored by an external device, motion correction can be applied directly to the individual LOR's in the list mode data stream. Uniform noise will reduce potential errors in the detection of small tumors, particularly when the tumor lies in an overlap region with high noise levels such as is encountered in the abdomen. Despite its desirable properties, continuous bed motion and monitoring of patient movement in whole-body scans has never been implemented for any PET scanner.

From the foregoing description, it will be recognized by those skilled in the art that a combined PET and X-Ray CT tomograph offering advantages over the prior art has been provided. Specifically, the combined PET and X-Ray CT tomograph provides a tomograph for acquiring CT and PET images sequentially in a single device, overcoming alignment problems due to internal organ movement, variations in scanner bed profile, and positioning of the patient for the scan. An improvement to both the CT-based attenuation correction procedure and the uniformity of the noise structure in the PET emission scan is also provided. The PET/CT scanner includes an X-ray CT and two arrays of PET detectors mounted on a single support within the same gantry, and rotate the support to acquire a full projection data set for both imaging modalities. The tomograph acquires functional and anatomical images which are accurately co-registered, without the use of external markers or internal landmarks.

While the present invention has been illustrated by description of several embodiments and while the illustrative embodiments have been described in considerable detail, it is no the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of the general inventive concept.

Having thus described the aforementioned invention, we claim:

1. A method for acquiring PET and CT images, comprising the steps of:
   placing a patient on a patient support;
   moving said patient support to position the patient within a CT scanner patient gantry such that a selected region of said patient to be imaged is within a field of view of a CT scanner associated with said CT scanner patient gantry;
   acquiring CT image data of the selected region of the patient;
   moving said patient support to position the patient within a PET scanner patient gantry such that said selected region to be imaged is within a field of view of a PET scanner associated with said PET scanner patient gantry;
   acquiring PET image data of the selected region of the patient;
   correcting said CT image data for artifacts due to field of view truncation, correcting said CT image data further comprising:
      obtaining non-corrected PET image data;
      determining a boundary of a truncated portion of the selected region of the patient using a non-corrected PET image reconstructed from said non-corrected PET image data;
      estimating a volume within said boundary of the truncated portion of the selected region using an average linear attenuation coefficient for the truncated portion of the selected region; and
      adding said volume to said CT image data;
   reconstructing a CT image from said corrected CT image data; and
   reconstructing a PET image from said acquired PET image data and using said corrected CT image data in the reconstruction of said PET image, to achieve a reconstructed PET image.

2. The method of claim 1, further comprising the step of continuously moving said patient support in an axial direction within said PET scanner patient gantry, whereby normalization effects between individual detector rings of said PET scanner are eliminated.

3. The method of claim 1 wherein said CT scanner patient gantry is separate from and fixed relative to said PET scanner patient gantry, said patient support being movable between said CT scanner patient gantry and said PET scanner patient gantry, whereby said step of acquiring CT image data of the selected region of the patient is accomplished within said CT scanner patient gantry, and whereby said step of acquiring PET image data of the selected region of the patient is accomplished within said PET scanner patient gantry.

4. The method of claim 1 wherein said CT scanner patient gantry is separate from said PET scanner patient gantry, wherein at least one of said CT scanner and said PET scanner is movable with respect the other, and wherein said patient support is movable between said CT scanner patient gantry and said PET scanner patient gantry, whereby said step of acquiring CT image data of the selected region of the patient is accomplished within said CT scanner patient gantry, and whereby said step of acquiring PET image data of the selected region of the patient is accomplished within said PET scanner patient gantry.

5. The method of claim 4 wherein said step of moving said patient support to position the patient within said CT scanner patient gantry is accomplished by moving said CT scanner to receive said patient bed within said CT scanner patient gantry.

6. The method of claim 4 wherein said step of moving said patient support to position the patient within said PET scanner patient gantry is accomplished by moving said PET scanner to receive said patient bed within said PET scanner patient gantry.

7. The method of claim 4, further comprising the step of continuously moving said patient support in an axial direction within said PET scanner patient gantry, whereby normalization effects between individual detector rings of said PET scanner are eliminated.

8. The method of claim 1 further including the step of displaying at least one of said reconstructed CT image and said reconstructed PET image.

9. The method of claim 1 further including the step of fusing said reconstructed CT image and said reconstructed PET image to achieve a fused PET/CT image.

10. A method for acquiring PET and CT images as set forth in claim 1, further comprising the step of:
generating attenuation correction factors for said PET image from said acquired CT image data and using said attenuation correction factors to reconstruct a corrected PET image.

11. The method of claim 10 wherein said step of generating attenuation correction factors from said reconstructed CT image is performed using the steps of:
estimating an attenuation image at 511 keV using a threshold to separate out a bone component of said reconstructed CT image; and
scaling said bone component using a first scaling factor and a non-bone component of said reconstructed CT image using a second scaling factor.

12. The method of claim 10 further including the step of displaying at least one of said reconstructed CT image and said attenuation-corrected PET image.

13. The method of claim 10 further including the step of fusing said reconstructed CT image and said attenuation-corrected PET image to achieve a fused PET/CT image.

14. The method of claim 10, further comprising the step of continuously moving said patient support in an axial direction within said PET scanner patient gantry, whereby normalization effects between individual detector rings of said PET scanner are eliminated.

15. The method of claim 10 wherein said CT scanner patient gantry is separate from and fixed relative to said PET scanner patient gantry, said patient support being movable between said CT scanner patient gantry and said PET scanner patient gantry, whereby said step of acquiring CT image data of the selected region of the patient is accomplished within said CT scanner patient gantry, and whereby said step of acquiring PET image data of the selected region of the patient is accomplished within said PET scanner patient gantry.

16. The method of claim 10 wherein said CT scanner patient gantry is separate from said PET scanner patient gantry, wherein at least one of said CT scanner and said PET scanner is movable with respect the other, and wherein said patient support is movable between said CT scanner patient gantry and said PET scanner patient gantry, whereby said step of acquiring CT image data of the selected region of the patient is accomplished within said CT scanner patient gantry, and whereby said step of acquiring PET image data of the selected region of the patient is accomplished within said PET scanner patient gantry.

17. The method of claim 16 wherein said step of moving said patient support to position the patient within said CT scanner patient gantry is accomplished by moving said CT scanner to receive said patient bed within said CT scanner patient gantry.

18. The method of claim 16 wherein said step of moving said patient support to position the patient within said PET scanner patient gantry is accomplished by moving said PET scanner to receive said patient bed within said PET scanner patient gantry.

19. The method of claim 10 wherein said step of reconstructing said attenuation-corrected PET image is accomplished using a Fourier rebinning technique and then independently by an ordered-subset EM iterative reconstruction algorithm.

20. A method for acquiring PET and CT images as set forth in claim 1, further comprising the step of:
correcting said PET image data for scatter and using said scatter-corrected PET image data to achieve said reconstructed PET image.

* * * * *